United States Patent [19]

Almog

[11] Patent Number: 6,024,701
[45] Date of Patent: Feb. 15, 2000

[54] METHOD OF AND SYSTEM FOR ESTIMATING PLACENTA AND FETUS WELL BEING USING SYSTEM IDENTIFICATION TECHNIQUES

[75] Inventor: Yael Almog, Rosh Haiyin, Israel

[73] Assignee: T.A.O. Medical Technologies Ltd., Israel

[21] Appl. No.: 09/140,889

[22] Filed: Aug. 27, 1998

[51] Int. Cl.$^7$ ........................................................ A61B 5/00
[52] U.S. Cl. ............................ 600/300; 128/898; 600/301
[58] Field of Search ..................................... 600/300, 301, 600/304, 313, 338, 351, 376, 511, 481, 529; 128/898

[56] References Cited

U.S. PATENT DOCUMENTS

| | | | |
|---|---|---|---|
| 4,821,732 | 4/1989 | Lippes | 600/481 |
| 5,123,420 | 6/1992 | Paret . | |
| 5,425,362 | 6/1995 | Siker et al. | 600/511 |
| 5,433,204 | 7/1995 | Olson | 600/454 |
| 5,442,940 | 8/1995 | Secker et al. . | |
| 5,474,065 | 12/1995 | Meathrel et al. . | |
| 5,596,993 | 1/1997 | Oriol et al. . | |
| 5,623,939 | 4/1997 | Garfield . | |

OTHER PUBLICATIONS

Loyke, HF, "Cold Pressor Test as a Predictor of the Severity of Hypertension", *South–Med–J.*, 88(3):300–304, 1995 (abstract).

Chang et al, "The Analysis of Relationship Between Fetal Stress and Blood Dynamics in Fetal Vessals", *Chung–Hua–Fu–Chan–Ko–Tsa–Chih*, 31(1): 15–7, Jan. 96. (abstract).

Chon et al, "Linear and Nonlinear System Identification of Autonomic Heart–Rate Modulation", *IEEE Engineering in Medicine and Biology*, pp 96–104, 1997.

North et al, "Uterine Artery Doppler Flow Velocity Waveforms in the Second Trimester for the Prediction and Fetal Growth Retardation", *Obstetrics & Gynecology*, 83(3): 378–386, 1994.

Gusdon et al, "A Clinical Evaluation of the "Roll–Over Test" for Pregnancy–induced Hypertension", *Am. J. Obstet. & Gynecol.*, 127(1): 1–3, 1977.

Eneroth–Grimfors et al, "Evaluation of Three Simple Physiologic Tests as Predictors of Pregnancy–Induced Hypertension", *Acta Obstet Gynecol Scand.*, 67: 109–113, 1988.

Peck, TM, "A Simple Test for Predicting Pregnancy–Induced Hypertension", *Obstetrics & Gynecology*, 50(5): 615–617, 1977.

Anderson, GJ, "The Roll–Over Test as a Screening Procedure for Gestational Hypertension", *Aust. & N.Z. J. of Obstet, and Gyn.*, 20: 144–146, 1980.

Baker et al, "The Use of the Hand–Grip Test for Predicting Pregnancy–Induced Hypertension", *Europ. J. of Obstet. & Gynecol. & Repro. Biol.*, 56: 169–172, 1994.

Degani et al, "Isometric Exercise Test for Predicting Gestational Hypertension ", *Obstetrics & Gynecology*, 65(5): 65–654, 1985.

Fairlie, Fmc, "Doppler Flow Velocimetry in Hypertension in Pregnancy", *Clinics in Perinatology*, 18(4): 749–777, 1991.

(List continued on next page.)

*Primary Examiner*—Eric F. Winakur
*Attorney, Agent, or Firm*—Mark M. Friedman

[57] ABSTRACT

System and screening method for determining characteristics of placenta and fetus in pregnant woman by using system identification techniques to determine whether a fetus is at immediate risk or should enter a high risk pregnancy follow-up. In particular, a system which is a combination of non invasive detectors for the acquisition of physiological signals, a procedure for synchronizing the acquired maternal and fetal signals, and algorithms developed for system identification of biological open-loop systems are employed. The maternal-fetal system has a purely causal relationship between input and output, connected by the placenta. Hence, the identification and modeling of the system reflect the interconnection relations.

19 Claims, 10 Drawing Sheets

OTHER PUBLICATIONS

Badalian, SS, "Nature and Mechanism of Hemodynamic Changes in Fetuses of Mothers with Various Types of Diabetes Mellitus", *Akush–Ginekol–Mosk,* 1989 Sep. (9): 39–42 (abstract).

Jung L, "System Identification Theory for the User", Prentice–Hall, Englewood Cliifs, N.J., Ed. T. Kon Lath, 1987, Chap 1, pp 69–89.

Wiener, N., "Nonlinear Problems in Random Theory", New York, Wiley, 1958 pp1–15.

Marmarelis, VZ., "Identification of Nonlinear Biological Systems Using Laguerre Expansions of Kernels", *Annals of Biomedical Engineering,* 21:573–589, 1993.

Lee et al "Measurement of the Wiener–Kernels of a Non–linear System by Cross–correlation", *Int J. Control,* 2: 237–254, 1965.

Sibai, BM, "Diagnosis and Management of hronic Hypertension in Pregnancy", *Obstetrics & Gynecology,* 78(3): 451–461, 1991.

Nylund et al, "Uteroplacental Blood Flow in Diabetic Pregnancy: Measurements with indium 113m and a computer–linked gamma camera", *Am. J. Obstet. Gynecol.,* 144: 298–302, 1982.

Branch et al, "Obstetric Complications Associated with the Lupus Anticoagulant", *New England J. of Medicine,* 313: 1322–1325, 1985.

Figure 5

*Pre-processing procedure:*
- Examine the data,
- Synchronize the various signals obtained from maternal origin as well as fetal origin,
- Filter the data,
- Decimate the data to the optimal sampling rate chosen for that specific signal,
- Divide the data into non-overlapping segments, ★     Beginning of External Manipulation ★★    End of External Manipulation Figure 8D          Box-Jenkins model $$y(t) = \frac{B_1(q)}{F_1(q)} u_1(t-nk) + \frac{B_2(q)}{F_2(q)} u_2(t-nk) + \frac{C(q)}{D(q)} e(t)$$

$y(t)$ - Output Signal (Fetal Heart Rate).

$u_1(t)$ - First Input Signal (Maternal Heart Rate).

$u_2(t)$ - Second Input Signal (Maternal PPG).

$e(t)$ - Noise.

$B_1(q)$, $F_1(q)$, $B_2(q)$, $F_2(q)$, $C(q)$, $D(q)$ - Polynoms in $q$.

Figure 8E          Parameters of the Model fitted to the Data

$B_1(q) = -3.198 \cdot 10^{-3} q + 0.3323 \cdot 10^{-3}$ $B_2(q) = -4.753 \cdot 10^{-5} q + 4.821 \cdot 10^{-5}$ $F_1(q) = q^2 - 1.947 q + 0.980$ $F_2(q) = q^2 - 1.995 q + 0.996$ $C(q) = q^2 + 0.0052 q - 0.165$ $D(q) = q^2 - 1.937 q + 0.946$

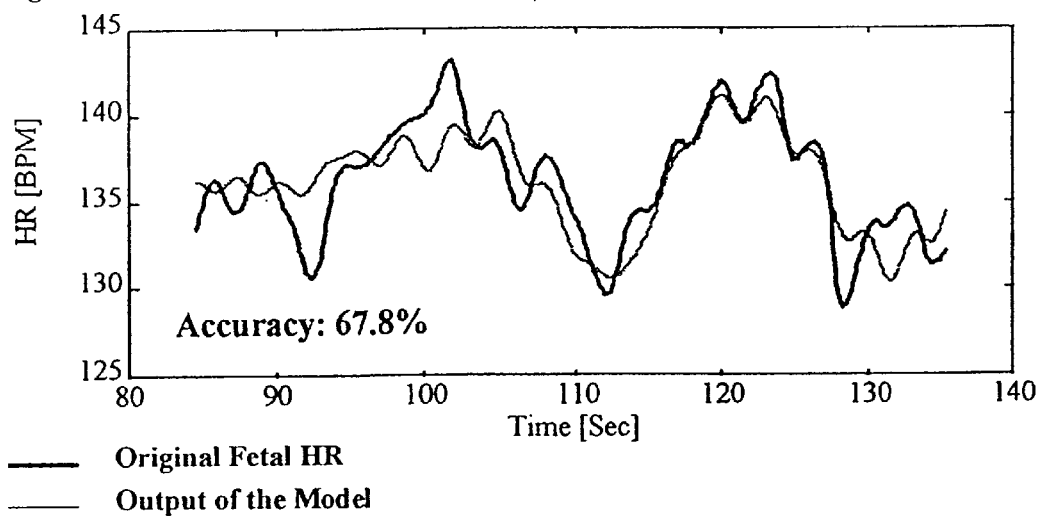

Figure 8F          Fetal Heart Rate, measured and simulated

——— Original Fetal HR
- - - Output of the Model

METHOD OF AND SYSTEM FOR ESTIMATING PLACENTA AND FETUS WELL BEING USING SYSTEM IDENTIFICATION TECHNIQUES

FIELD AND BACKGROUND OF THE INVENTION

The present invention relates to a method and system for evaluating the condition of the placenta in pregnant women as well as the well being of the fetus and/or the mother by using physiological parameters and system identification methods. The invention is particularly applicable for estimating the functionality and well being of the placenta and fetus from the second trimester on.

Medical Background

It has become an increasing practice in obstetrics to evaluate the well being of the baby while it is still in utero. This practice called anterpartum testing, has been extensively practiced since the early 1970 on certain high risk obstetrical patients. One of the uses of anterpartum testing is to determine how well the placenta is supplying the needed oxygen and nutrients to the growing fetus, and removing fetal wastes thefrom.

Almost 70% of fetal deaths occurs before the onset of labor. Antepartum fetal death accounts for nearly 40% of all perinatal mortality in the United States. The majority of fetal deaths occur before 32 week's gestation.

Antepartum fetal deaths may be divided into four broad categories: (i) chronic asphyxia of diverse origin; (ii) congenital malformations; (iii) superimposed complications of pregnancy, such as Rhesus isoimmunization, placental abruption, hypertension, diabetes and fetal infection; and (iv) deaths of unexplained cause.

Based on available data, approximately 30% of antepartum fetal deaths may be attributed to asphyxia, 30% to maternal complications, especially placenta abruption, hypertension, and preeclapmsia, 15% to congenital malformations and chromosomal abnormalities, and 5% to infection.

A large clinical experience has demonstrated that antepartum fetal assessment can have a significant impact on the frequency and cause of fetal deaths.

Indications for antepartum fetal monitoring in patients known to be at risk of utero-placental insufficiency include maternal, fetal, placental and background indications. Maternal indications include prolonged pregnancy; diabetes mellitus; hypertension and advanced maternal age. Fetal indications include: suspected IUGR (intrauterine growth restriction) and decreased fetal movements. Placental indications include: abruption of the placenta and abnormal amniotic fluid. Background indications include: previous stillbirth.

The fetus and the placenta depend upon unique physiological systems to provide an environment supporting fetal growth and development.

To appreciate the complexity of the placenta as a transfer organ, it is necessary to point out that the placenta provides the fetus with products that are essential for its well being including essential nutrients, fluid and oxygen, and it serves as a route for clearance of fetal excretory products [1].

The transport characteristics of the placenta allow respiratory gases and many solutes to reach equal concentration between the maternal intervillous space blood and fetal capillary blood. Thus, the rate of blood flow in these two circulations is important in the determination of fetal oxygen and nutrient supply. Over the course of a normal singleton gestation, uterine blood flow increases more than 50-fold above non-pregnant values. Two factors contribute to this dramatic increase in blood flow: placental growth and maternal arterial vasodilatation.

The uterine artery behaves as a nearly maximally dilated system. Fetal blood flow to the umbilical circulation represents approximately 40% of the fetal cardiac output. During the 1st trimester, increases in umbilical blood flow are proportional to fetal growth.

Many maternal organs undergo physiological changes during the course of pregnancy. Maternal cardiac output, the product of heart rate and stroke volume, increases about 30–50% during pregnancy. The distribution of maternal cardiac output changes as pregnancy progresses. In the first trimester the uterus receives 3% of the cardiac output, however it receives 17% of the cardiac output near term. The percentage of cardiac output devoted to kidney, brain and skin is not dramatically altered by pregnancy. Peripheral vascular resistance falls during pregnancy. The cause for this is the smooth muscle relaxing effect of high progesterone levels associated with the pregnancy. There is a progressive rise in venous pressure in the lower extremities.

The placenta, the mother and the fetus make important contribution to the immunological maintenance of pregnancy.

Advances in perinatal and neonatal health care have resulted in a substantial reduction in perinatal mortality. These improvements primarily relate to better capabilities in treating maternal diseases during pregnancy, advance in neonatal care and may also be due to improvements in antepartum fetal surveillance techniques.

There are some medical conditions in pregnancy that may lead to poor placental functioning such as diabetes, hypertension, anemia and prolonged pregnancy. In these conditions it is of great importance to evaluate the placental functioning. For these or other indications obstetrician will determine whether one is in need to have anterpartum testing during the pregnancy.

Antepartum fetal testing is a term that embraces data from fetal movement counts to biophysical monitoring methods, such as contraction stress test, nonstress test, fetal biophysical monitoring profile, amniotic fluid assessment, Doppler velocimetry, vibro-acoustic fetal stimulation and computerized fetal heart rate.

The following lists few of the tests used for fetal monitoring.

Antepartum fetal heart rate testing (non stress test, NST): In NST, fetal heart rate acceleration in response to fetal movement are recorded via electronic equipment on a strip of paper.

Cardiotocography (CTG): CTG utilizes electronic equipment to record the fetus' heart rate pattern. Uterine contractions, if present are also registered. This information is recorded on a strip of paper, producing a tracing that is read by the obstetrician. Certain changes in the fetal heart rate pattern can signal a problem.

Amniotic Fluid Index (AFI): The amount of amniotic fluid surrounding the fetus may be decreased in some high-risk pregnancies. The amount of amniotic fluid present is measured by ultrasound scanning.

Fetal Biophsical Profile (FBP): The CTG trace is obtained and then four parameters are observed by ultrasound. The four parameters are fetal tone, fetal movements, fetal breathing, and the amniotic fluid index. Not all of these tests need to be performed at the same time.

Since there are many different pathophysiological processes leading to fetal asphyxia, indication-specific testing is reasonable and it may allow early identification of at-risk fetuses. The FBP is useful in the detection of developing fetal asphyxia even before it irreversibly affects the fetus.

No program of antepartum fetal testing can completely remove the risk of fetal death. The most appropriate antepartum tests appear to be amniotic fluid volume assessment, fetal tone and fetal heart monitoring.

The use of Doppler ultrasound is not beneficial in most clinical cases. The single most effective test that distinguishes normal-small from compromised small fetuses is the determination of the umbilical artery Doppler waveform.

Doppler velocimetry seems to be reliable in diagnosing conditions predisposing to IUGR such as chronic hypertension, collagen vascular disorders, and other diseases in which vasospasm plays a major role.

Hence, it remains uncertain which is the optimal Doppler ultrasound measurement of the uteroplacental circulation to obtain the best sensitivity and predictive values for evaluation of fetal and placental pathologies such as preeclampcia and IUGR [2].

The usual decrease in utheroplacental blood flow associated with uterine contraction, when superimposed with chronic utheroplacental insufficiency (e.g., diabetes associated with vascular changes, postdatism) may result in acute fetal distress.

In contrast, maternal hypotension (e.g., after induction of spinal or epidural anesthesia) can cause acute fetal distress despite the presence of a normal utheroplacental unit. Furthermore, maternal positioning has a strong influence on the condition of the fetus.

There are strong indications that the utheroplacental unit has specific characteristics which can be evaluated by a variety of external manipulations [3–13].

There is no doubt that better objective and advanced measures of placenta well being and fetal asphyxia and asphyxia-related morbidity are needed to allow for a more scientific approach of antenatal fetal surveillance.

Mathematical Background

A system is an object in which different kind of variables interact and produce observable signals [14]. The observable signals that are of interest are usually referred to as "outputs". The system is also affected by external stimuli. External signals that can be manipulated by the observer are referred to as "inputs". Others are referred to as "disturbances" and can be divided into those that are directly measured and those that are only observed through their influence on the output. The distinction between inputs and measured disturbances is often less important for the modeling process.

Clearly, the notion of a system is a broad concept and plays an important role in modern science. Dynamic systems are those for which the current output value depends not only on the current external stimuli but also on earlier values.

When one interacts with a system, one needs to have a concept of how the system's variables relate to one another. With a broad definition, the relationship among observed signals is referred to as "a model of the system". Models can come in various shapes with varying degree of mathematical formalism. The intended use determines the degree of sophistication that is required to make the model purposeful.

Mathematical models describe the relationship among system variables in terms of mathematical expressions like difference or differential equations. Mathematical models may be characterized by a number of adjectives (time continuous or time discrete, lumped or distributed, deterministic or stochastic, linear or nonlinear, etc.) signifying the type of differential equation used.

Basically, a model has to be constructed from observed data. Mathematical models may be developed along two routs.

One route is to split the system into subsystems, whose properties are well understood from previous experience. These subsystems are then joined mathematically and a model of the whole system is obtained. This route is known as "Modeling", and does not necessarily involve any experimentation on the actual system.

The other route to mathematical as well as graphical models is directly based on experimentation. Input and output signals from the system, are recorded and subjected to data analysis in order to infer a model. This route is known as "System Identification", the final outcome of which is a model of the system under study.

System identification is the subject of constructing or selecting models of dynamic systems to serve certain purposes. A first step is to determine a class of models within which the search for the most suitable model is to be conducted. A model of a system is a description of its properties, suitable for a certain purpose. The model need not be a true and accurate description of the system, nor need the user believe it to be so, in order to serve its purpose.

Quiet often it is not possible to determine, apriori, the coefficients characterizing the system from knowledge of the physical mechanisms that govern the system's behavior. Instead, the determination of all or some of them must be left to estimation procedures. The model thus becomes a set of models and it is for the estimation procedure to select that member in the set that appears to be the most suitable for the purpose in question.

The procedure to determine a model of a dynamic system from observed input-output data involves four basic ingredients [14]:

1. The data: The input-output data which are recorded during a specific designed identification procedure.

2. A set of candidate models: A set of candidate models is obtained by specifying within which collection of models one is going to look for a suitable one.

3. A rule by which candidate models can be assessed using the data: This is the identification method, and is based on the performance of the model when one attempts to reproduce the measured data. A deficient model in these respects makes one reject the model, while good performance will develop a certain confidence in the model.

4. The procedure of identification is repeated for nonoverlapping segments of each set of data, in order to evaluate the accuracy of the model and the confidence level of the results.

However, a model can never be regarded as a final and true description of the system. It can at best be regarded as a good enough description of certain aspects of particular interest.

The present invention is based on the broad concept of system identification, using the relationship between mother and fetus as an input-output open-loop system connected by a connection function. System identification deals with the problem of building mathematical models of dynamic systems, based on observed data. The area has matured into an established collection of basic techniques that are well understood and known to be successfully performed in practical applications [14]. Since the mother and fetus are connecting solely via the placenta, the present invention enables placental and fetal functionality assessment.

There is thus a widely recognized need for, and it would be highly advantageous to have, a method and system for evaluating the condition of the placenta in pregnant women as well as the well being of the fetus by using physiological parameters and system identification methods.

SUMMARY OF THE INVENTION

According to one aspect of the present invention there is provided a method of diagnosis of malfunction of a placenta and fetus in a pregnant woman having a maternal-placenta-fetal system.

According to further features in preferred embodiments of the invention described below, the method comprising the steps of (a) simultaneously monitoring selected maternal and fetal physiological signals; (b) identifying a model describing the maternal-placenta-fetal system, and parameters describing the model; and (c) determining, is according to the model and the parameters describing the model, the well being of the placenta.

According to another aspect of the present invention there is provided a method of diagnosis of pathologies of a fetus in a pregnant woman having a maternal-placenta-fetal system, the method comprising the steps of (a) simultaneously monitoring selected maternal and fetal physiological signals; (b) identifying a model describing the maternal-placenta-fetal system, and parameters describing the model; and (c) determining, according to the model and the parameters describing the model, the well being of the fetus.

According to still another aspect of the present invention there is provided a method of diagnosis of a maternal-fetus relation in a pregnant woman having a maternal-placenta-fetal system, the method comprising the steps of (a) simultaneously monitoring selected maternal and fetal physiological signals; (b) identifying a model describing the maternal-placenta-fetal system, and parameters describing the model; and (c) determining, according to the model and the parameters describing the model, the maternal-fetus relation.

Further according to the present invention there is provided a system for effecting the above methods, the system is thus for monitoring a pregnancy in a pregnant woman having a maternal-placenta-fetal system and comprising (a) at least one monitoring device for simultaneously monitoring selected maternal and fetal physiological signals; and (b) a computerized system being in communication with each of the at least one monitoring devices for identifying a model describing the maternal-placenta-fetal system, and parameters describing the model.

According to still further features in the described preferred embodiments while simultaneously monitoring the selected maternal and fetal physiological signals the pregnant woman experiences a provoked external stimulus.

According to still further features in the described preferred embodiments the physiological signals are selected from the group consisting of ECG, BP, $PO_2$, $PCO_2$, blood flow, blood velocity, blood volume, heart rate, systolic blood pressure, diastolic blood pressure, systolic/diastolic blood pressure ratio, resistance index, pulsatility index, thermal index and other Doppler flow indexes.

According to still further features in the described preferred embodiments the model is selected from the group consisting of wherein said model is selected from the group consisting of nonparametric models, parametric models, polynominal representation, simple autoregressive model, ARMAX model structure, output error structure, Box-Jenkins model structure, general parametric model structure, state space representation, linear time-varying models, time-invariant model, nonlinear models, nonlinear ARMAX, Wiener kernels model, Korenberg-Billings model and Volterra-Wiener model.

According to still further features in the described preferred embodiments the model is a best model describing the maternal-placenta-fetal system, the best model is selected out of a plurality of available models and according to predetermined criteria, including technical conciderations, such as, but not limited to, memomery comciderations, accuracy required, and conciderations relating to computing power optimization.

Thus, the present invention is based on the broad concept of system identification, and more particularly on using the relationship between mother and fetus as an input-output open-loop system connected by a connection function.

The present invention successfully addresses the shortcomings of the presently known configurations by providing a method and system for evaluating the condition of the placenta in pregnant women as well as the well being of the fetus by using physiological parameters and system identification methods.

BRIEF DESCRIPTION OF THE DRAWINGS

The invention herein described, by way of example only, with reference to the accompanying drawings, wherein:

FIG. 5 describes the preprocessing steps;

FIGS. 8a–8f is an example of model determination for steady state conditions.

DESCRIPTION OF THE PREFERRED EMBODIMENTS

Figure 1:
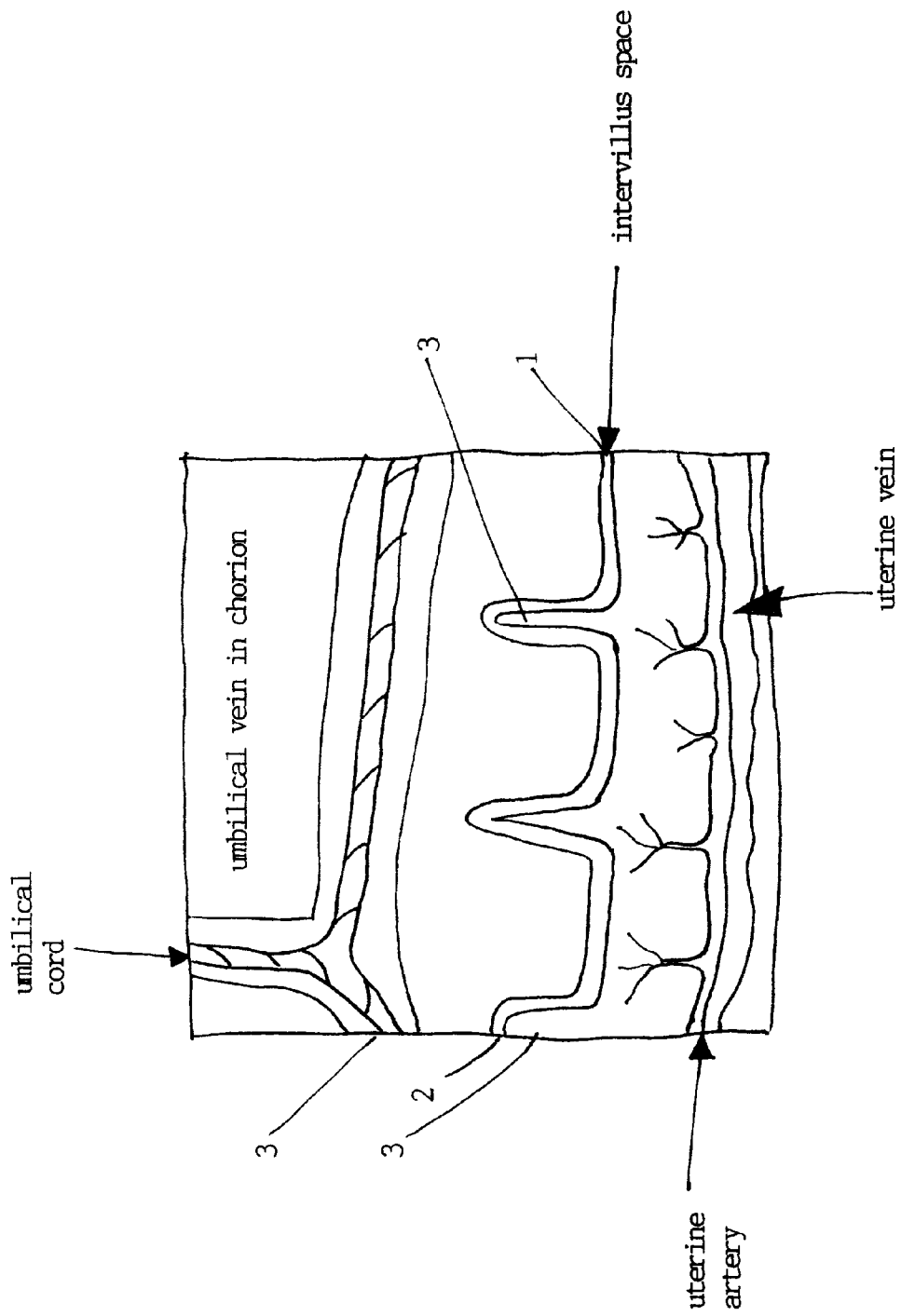
FIG. 1 is a schematic diagram of the maternal-placental-fetal circulation unit.

The present invention is of a method and system for evaluating a pregnant women which can be used for evaluating the condition of the placenta, as well as the well being of the fetus by using physiological parameters and system identification methods. Specifically, the present invention can be used to detect pathologies associated with placental functioning long before a measurable pathology is detectable in the mother or fetus.

The principles and operation of a method and system according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

According to a broad aspect of the present invention, there is provided a method of evaluating the placental-fetal-maternal conditions in pregnant women. The evaluation is performed according to the following steps.

First, selected maternal and fetal physiological signals are simultaneously monitored.

Second, a model describing the maternal-placenta-fetal system and parameters describing the model are identified. The model and its parameters collectively define a connection function connecting the input (e.g., measured maternal physiological signals) and the output (e.g., simultaneously measured fetus physiological signals) or in other words describing the maternal-placenta-fetal system.

Third, according to the model and the parameters describing the model, the placental-fetal-maternal conditions are evaluated, e.g., as normal or abnormal (e.g., pathological).

Preferably the input is chosen as the maternal signals and the output as the fetus signals. However, the method can also be performed when changing the roles of the input-output, giving parameters which have no physiological meaning.

It will thus be appreciated that the present invention is based on the broad concept of system identification, using the relationship between the mother and the fetus as an input-output open-loop system connected by a connection function.

As is strongly evident from the literature cited [3–13], there is a strong correlation between maternal and fetus parameters in various pathophysiological conditions. It is therefore clearly anticipated and it is further shown hereinunder that the mother-placenta-fetus behave as a dynamic system.

System identification deals with the problem of building mathematical models of dynamic systems, based on observed data. The area has matured into an established collection of basic techniques that are well understood and known to be successfully performed in practical applications [14]. The identification of models from data involves decision making while searching for a suitable model. One needs to go through several iterations along the process of arriving to a final model, where at each step previous decisions are revised. There are various techniques for system identification problems ranging from simple linear models to linear models with noise and more complicated nonlinear models, some of which are described in greater detail hereinunder.

Referring now to the drawings, FIG. 1 shows a schematic diagram of the maternal-placental-fetal circulation units. Maternal blood flows in the uterine blood circuit close to exchange surface 1, whereas fetal blood flows in the placental blood circuit close to exchange surface 1, such that maternal nutrients and oxygen present in the maternal blood cross the intervillous space 2 into the capillaries of the chorionic villi 3, whereas fetal waste products cross space 2 into the maternal blood.

Figure 2:
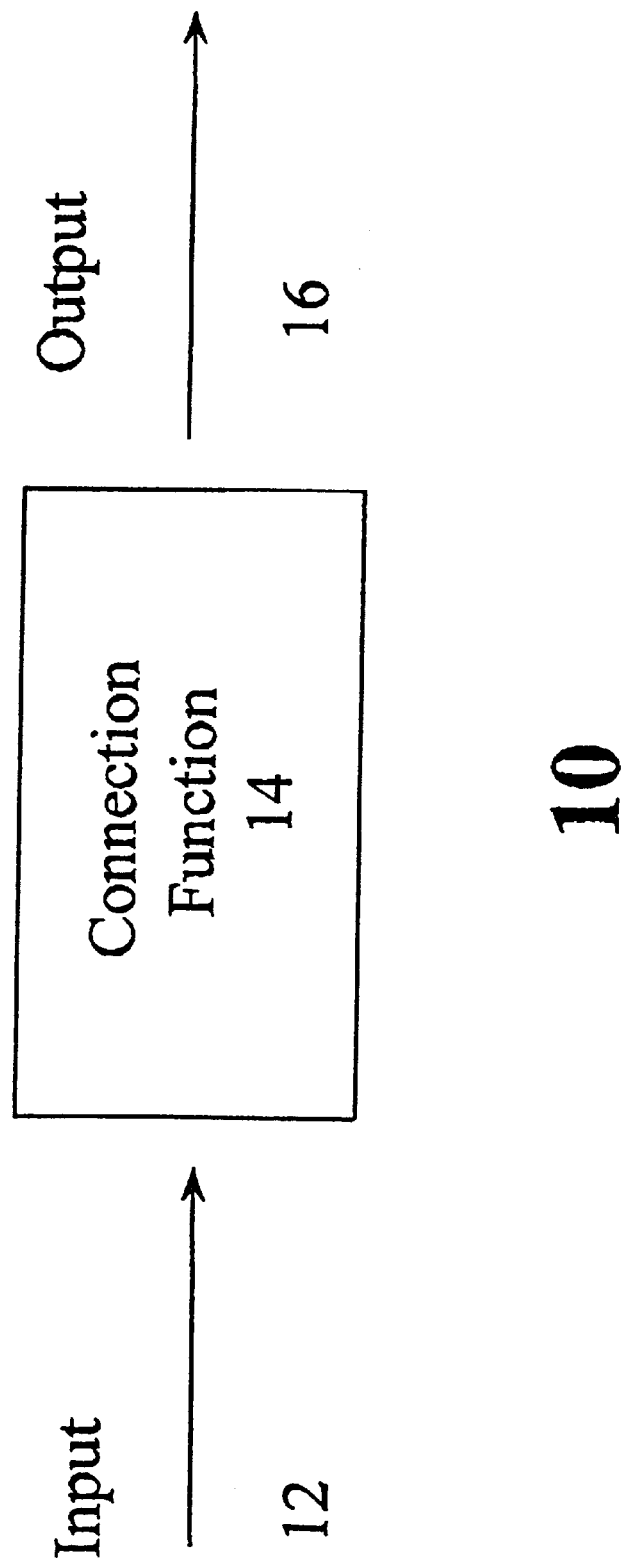
FIG. 2 is a block diagram of the basic concept in accordance with the teachings of the present invention.

FIG. 2 is a basic block diagram of a dynamic system 10 according to the present invention describing a maternal-placenta-fetus system. System 10 features maternal input or inputs 12, a connection function 14 (i.e., model and model parameters), and fetus output or outputs 16. Connection function 14 is selected to best connect between input or inputs 12 and output or outputs 16.

Figure 3:
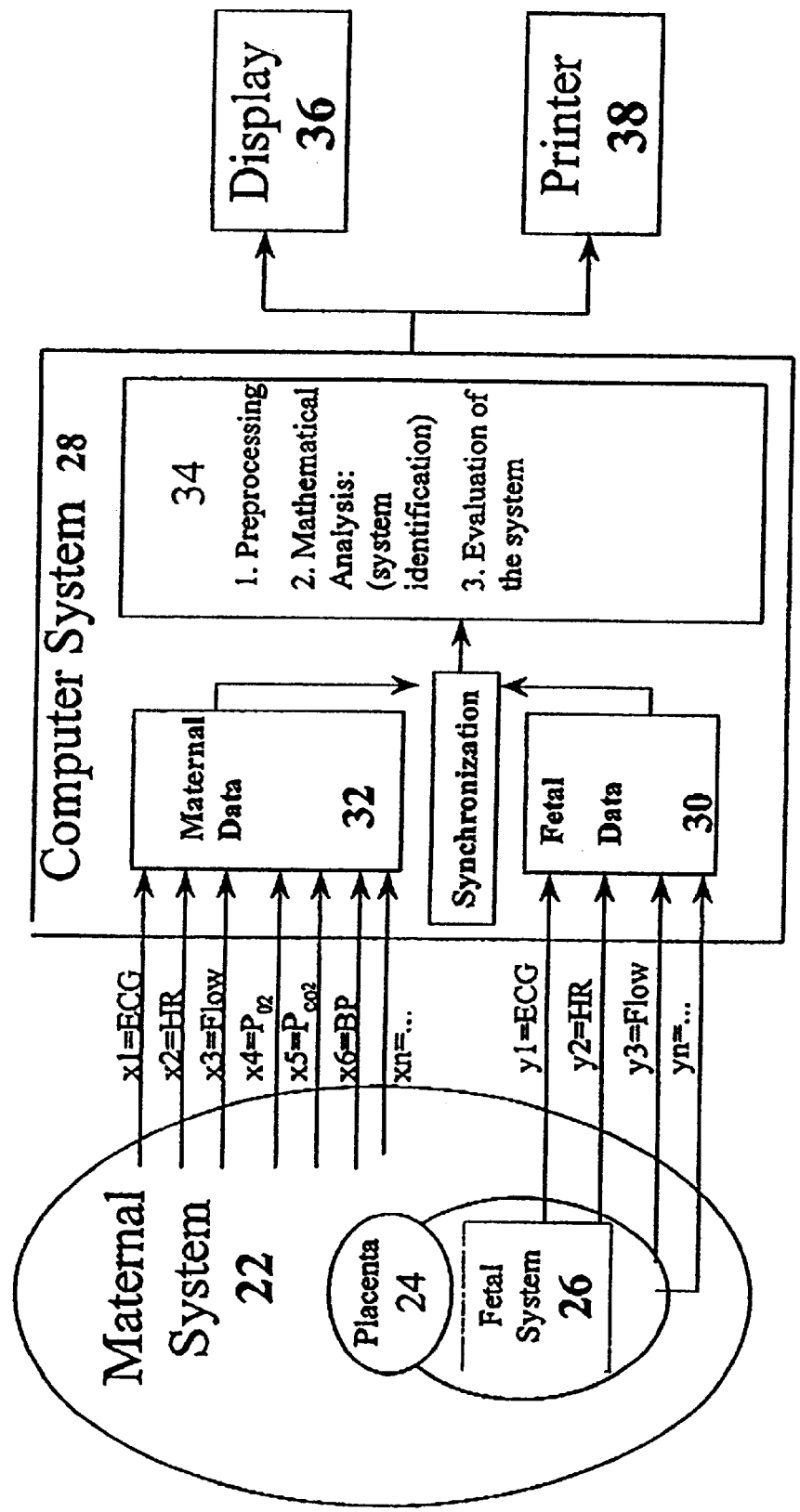
FIG. 3 is a block diagram of an exemplary system for analyzing signals of the maternal-fetal dynamic system according to the present invention.

FIG. 3 is a block diagram of an exemplary system 20 in accordance with the teachings of the present invention. The present invention may be used to evaluate a placenta 24, which is the connecting organ between the mother and the fetus, using signals derived from the maternal system 22, and the fetal system 26.

Maternal physiological parameters un, such as ECG, BP, $PO_2$, $PCO_2$, blood flow, blood velocity and blood volume or pseudo physiological signals, such as heart rate—HR, systolic blood pressure—S, diastolic blood pressure—D, resistance index—RI, pulsatility index—PI, or others, such as S to D ratio, etc., and fetal physiological parameters yn, such as ECG, $PO_2$, $PCO_2$, blood flow, blood velocity and blood volume, or pseudo physiological signals, such as HR, S, D, RI, PI, S/D, etc., are simultaneously recorded using maternal 32 and fetus 30 suitable sensors or devices. If the pregnancy is of more than a single fetus (e.g., twins) separate monitoring may be performed for each of the fetuses by dedicated sensors.

Recordings of the physiological parameters may be effected by sensors or devices known in the art, such as, but not limited to, ultra-sound imaging devices, MRI, electromagnetic sensors and sound wave sensors. Others include those disclosed in, for example, U.S. Pat. Nos. 4,945,917; 5,596,993; 5,474,065; 5,442,940; 5,623,939; and U.S. Pat. No. 5,123,420, which are incorporated by reference as if fully set forth herein.

As a first step following data acquisition, preprocessing of the data is performed. To this end, a computer system 28 is provided and via an analog to digital converter (A/D) (when an analog signal is acquired) it creates discrete time series out of the various physiological parameter recordings.

The various signals, from maternal origin and fetal origin are then synchronized and filtered in order to remove trends and experimental noise.

Physiological parameters of the fetus may also be detected using maternal sensors, for example the determination of fetal HR from maternal ECG, see U.S. Pat. No. 4,945,917.

Computer system 28 then performs an iterative process to choose an optimal connection function 34. The characteristics of connection function 34, as well as the optimal connection fuinction type are evaluated.

The maternal-placenta-fetal systems 22, 24, 26 are described with the most adequate model parameters found. The results of the various estimations and characterizations of systems 22, 24, and 26 are then displayed using a display 36 or a printer 38.

The determined characteristics displayed or printed may be a number, numbers or a plot representative of the determined characteristics. These displays, plots, or numbers may be used by the physician for diagnosis.

Figure 4:
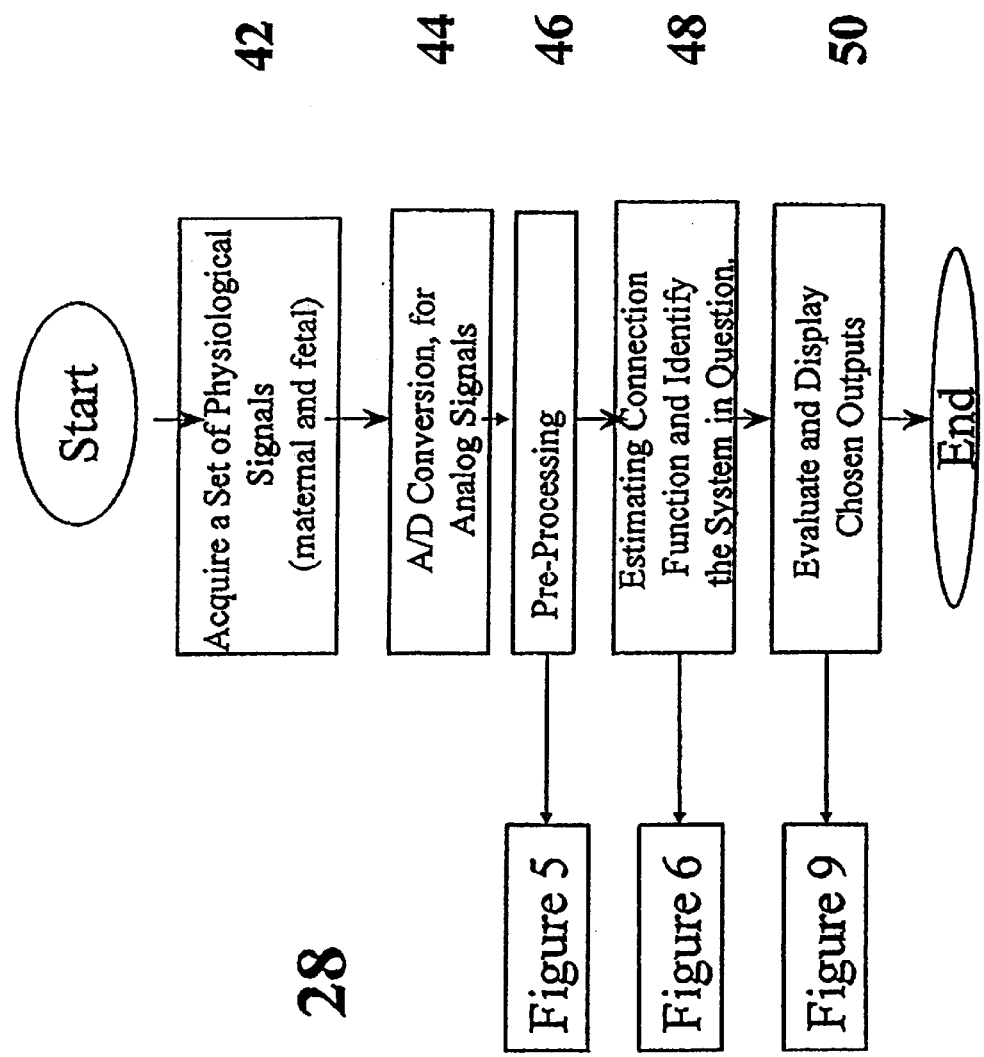
FIG. 4 is a flow diagram of a preferred embodiment of a method of analyzing signals from maternal/fetus system in accordance with the present invention.

Shown in FIG. 4, is a more detailed flow diagram describing the functionality of computer system 28. The first step 42, involves the acquisition of the physiological signals simultaneously taken from both the mother and the fetus.

Then, at step 44, AID conversion is performed for further computer analysis. Shown in step 46 (see also FIG. 5) are the preprocessing steps to prepare the input and output data. In step 48, an iterative computation is executed, using system identification techniques, at the end of which an adequate description of the dynamic system is obtained. In step 50 the outputs are evalated and optionally displayed. Further description of this step is provided hereiunder with reference to FIG. 9.

Figure 6:
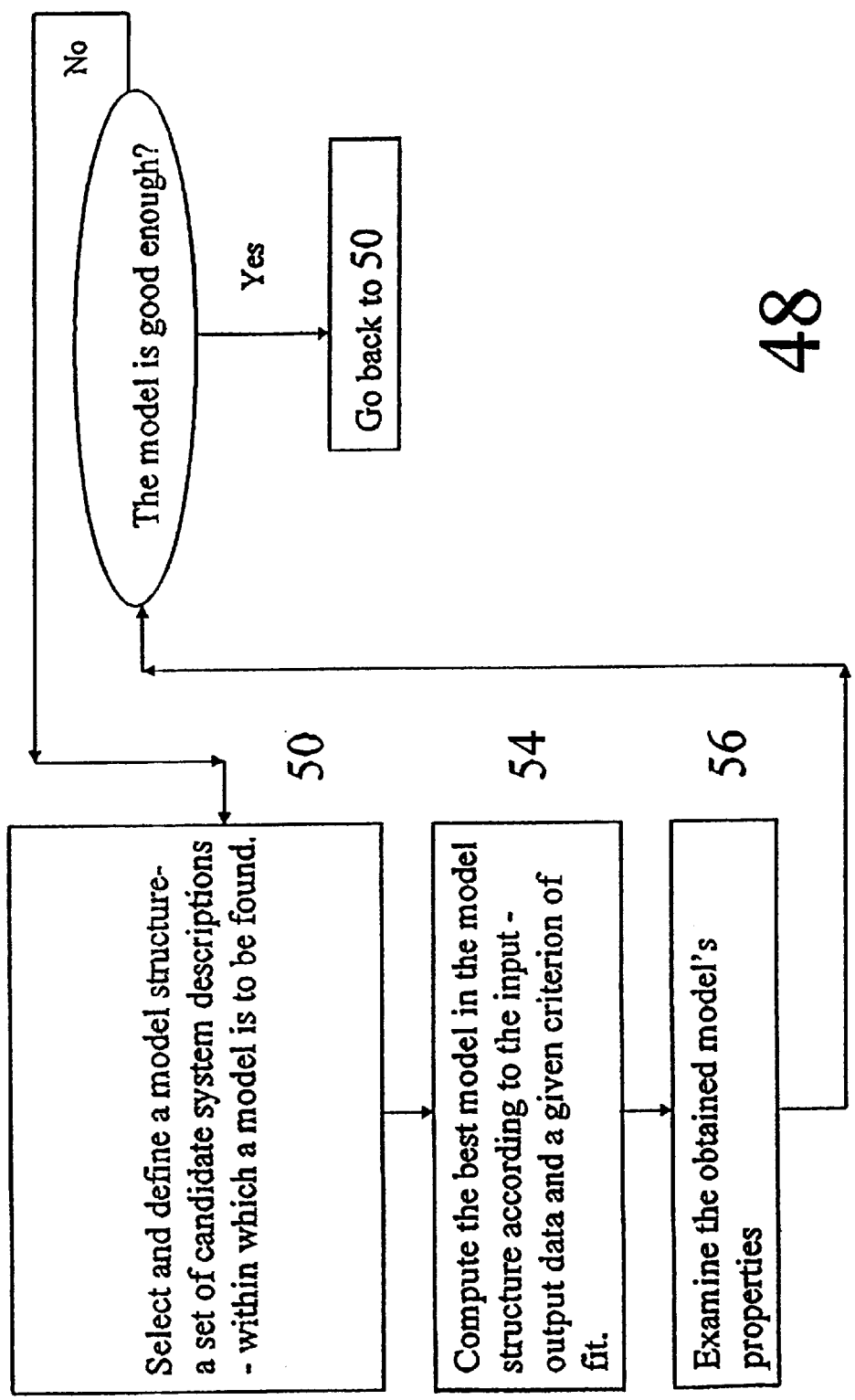
FIG. 6 is a flow diagram of the mathematical procedure performed in the identification process.

A detailed description of step 48 is presented in FIG. 6. There are various potential models to be used under step 52, a description of few is given hereinbelow:

I. Linear Time-Invariant System Identification a. Nonparametric models

For experimental data, the aim is to determine a set of functions by direct techniques without first selecting a confined set of possible models. Such methods are called nonparametric since they do not explicitly employ a finite-dimensional parameter vector in the search for the best description.

The nonparametric methods for describing linear models are composed of time-domain methods and frequency-domain methods of various degrees of sophistication.

Assuming that the input-output signals are related by a linear system, the relationship can be written:

$$y(t)=G(q)u(t)+\epsilon(t) \quad\quad 1.$$

where:

u(t): t=1,2 ... N is the input.

y(t): t=1,2 ... N is the output.

q is the shift operator and $$G(q)u(t) = \sum_{k=1}^{\infty} g(k)u(t-k) \quad\quad 2.$$

and $$G(q) = \sum_{k=1}^{\infty} g(k)q^{-k}; \quad q^{-1}u(t) = u(t-1) \quad\quad 3.$$

The numbers {g(k)} are called the impulse response of the system. g(k) is the output of the system at time k if the input is a single pulse at time zero.

The function G(q) is called the transfer function of the system.

When evaluated on the unit circle ($q=e^{iw}$) gives the frequency function:

$$G(e^{iw}) \quad\quad 4.$$

In Eq. 1 $\epsilon(t)$ is an additional unmeasurable disturbance, noise. Its properties can be expressed in terms of its auto spectrum:

$$\phi_v(\omega) = \sum_{\tau=-\infty}^{\infty} R_v(\tau)e^{-i\omega\tau} \quad\quad 5.$$

where $R_v(\tau)$ is the covariance function of $\epsilon(t)$. The disturbance $\epsilon(t)$ can also be described as filtered white noise:

$$\epsilon(t)=H(q)e(t) \quad\quad 6.$$

where e(t) is white noise with variance $\lambda$ and $$\phi_v(\omega)=\lambda|H(e^{i\omega})|^2 \quad\quad 7.$$

Eqs. 1 and 6 give a time domain description of the system, $$y(t)=G(q)u(t)+H(q)e(t) \quad\quad 8.$$

Eqs. 4 and 7 constitute a frequency domain description.

Both descriptions are called nonparametric model description since they are not defined in terms of a finite number of parameters. This basic description also applies to several input signals and several output signals.

b. Parametric models

Parameter estimation methods for linear models are based on the following procedure.

A set of candidate models must be selected, and parametrized as a model structure, using a vector $\theta$. The search for the best model within the set then becomes a problem of determining or estimating $\theta$ There are many different ways of organizing such a search and also different views on what one should search for.

Given a description (Eq. 8) and having observed the input-output data u(t), y(t) the predictor error e(t) can be computed as:

$$e(t)=H^{-1}(q)[y(t)-G(q)u(t)] \quad\quad 9.$$

These errors are, for a given u and y, functions of G and H. These in turn are parametrized by polynomial or by state space matrices.

(i) Polynomial representation

The functions G and H can be represented as a rational function of $q^{-1}$ and specify the numerator and denominator coefficients in some way. Such model structure are also known as black-box models.

A commonly used parametric model is the ARX (simple autoregressive model) that corresponds to:

$$G(q) = q^{-nk}\frac{B(q)}{A(q)}; H(q) = \frac{1}{A(q)} \quad\quad 10.$$

where B and A are polynomials in the delay operator $q^{-1}$:

$$A(q)=1+a_1q^{-1} \ldots +a_{na}q^{-1} \quad\quad 11.$$

$$B(q)=b_1+b_2q^{-1} \ldots +b_{nb}q^{-nb+1} \quad\quad 12.$$

The numbers na and nb are the orders of the respective polynomial. The number nk is the number of delays from input to output. The model is usually written:

$$A(q)y(t)=B(q)u(t-nk)+e(t) \quad\quad 13.$$

or $$y(t)+a_1y(t-1)+ \ldots +a_{na}y(t-na)=b_1u(t-nk)+b_2u(t-nk-1)+ \ldots +b_{nb}u(t+nk-nb+1)+e(t)$$

Eq. 13 applies also to several input signals and several output signals, where A(q) and the coefficients $a_i$ become nyxny matrix, B(q) and the coefficients $b_i$, becomes nyxnu.

A more complex parametric model is called ARMAX model structure:

$$A(q)y(t)=B(q)u(t-nk)+C(q)e(t) \quad\quad 14.$$

$$C(q)=p1+c_1q^{-1}+ \ldots +c_{nc}q^{-nc}$$

where A(q) and B(q) are defined in Eqs. 11 and 12.

An Output Error (OE) structure is obtained as:

$$y(t) = \frac{B(q)}{F(q)} u(t-nk) + e(t) \quad 15.$$

with $$F(q) = 1 + f_1 q^{-1} + \ldots + f_{nf} q^{-nf}$$

The so called Box-Jenkins (BJ) model structure is given by:

$$y(t) = \frac{B(q)}{F(q)} u(t-nk) + \frac{C(q)}{D(q)} e(t) \quad 16.$$

with $$D(q) = 1 + d_1 q^{-1} + \ldots + d_{nd} q^{-nd}$$

These models are special cases of the General parametric model structure:

$$A(q)y(t) = \frac{B(q)}{F(q)} u(t-nk) + \frac{C(q)}{D(q)} e(t) \quad 17.$$

with $$F(q) = 1 + f_1 q^{-1} + \ldots + f_{nf} q^{-nf}$$

and $$D(q) = 1 + d_1 q^{-1} + \ldots + d_{nd} q^{-nd}$$

Within the structure of Eq. 17, virtually all of the usual linear black box model structure is obtained. For example the ARX is obtained for nc=nd=nf=0, the ARMAX is obtained for nf=nd=0.

The structures discussed may give rise to 32 (25) different model sets, depending on which of the polynomials A, B, C, D and F are used. The same type of models can be defined for systems with an arbitrary number of inputs. They have the form:

$$A(q)y(t) = \frac{B_1(q)}{F_1(q)} u_1(t-nk_1) + \ldots + \frac{B_{nu}(q)}{F_{nu}(q)} u_{nu}(t-nk_{nu}) + \frac{C(q)}{D(q)} e(t) \quad 18.$$

The most complete description is that of a multivariable signals where the input (u) is an m-dimensional vector and the output (y) is a p-dimensional vector. The system is still given by:

$$y(t) = G(q, 6)u(t) + H(q, 6)e(t) \quad 19.$$

with $$G(q, 6) = A^{-1}(q)/B(q)$$

$$H(q, 6) = A^{-1}(q)$$

G(q,6) will be p×m matrix whose entries are rational functions of $q^{-1}$.

(ii) State space representation

In the state space the relationship between the input, noise, and output signals is written as a system of first-order differential or difference equations using an auxiliary state vector x(t).

For the purpose of system identification it is especially usefull in that insights into mechanisms of the system can usually be incorporated into state-space models than into other type of models.

The modeling usually leads to a representation:

$$u(t+1) = Ax(t) + Bu(t) \quad 20.$$

$$y(t) = Cx(t) + Du(t) + v(t) \quad 21.$$

Here the relationship between the input u(t) and the output y(t) is defined via the nx-dimensional state space vector x(t).

II. Linear time-varying System Identification

While linear, time-invariant models form the most common way for describing a dynamic system, it is also quiet often useful or necessary to employ other descriptions such as linear time-varying models.

A general linear system can then be described as:

$$y(t) = \sum_{k=1}^{\infty} g_1(k) u(t-k) + v(t) \quad 22.$$

and if one writes $$g_t(k) = \breve{g}(t, t-k) \quad 23.$$

one finds that $$y(t) = \sum_{s=-\infty}^{t-1} \breve{g}(t, s) u(s) + v(t) \quad 24.$$

where $$\breve{g}(t, s), t = s, s+1, \ldots,$$

is the response at time t to a unit pulse at time s.

The function $\breve{g}$ is also known as the "weighting function", since it describes the weight that the input at time s has on the output at time t. The description in Eq. 24 is quiet analogous to the time-invariant model, except that the sequence $g_t(k)$ carries the time index t.

In general a time-varying transfer function can be introduced as:

$$G_t(q) = \sum_{k=1}^{\infty} g_t(k) q^{-k} \quad 25.$$

and then repeat the procedures introduced above.

It is important to note that other linear system identification methods are available, such as time-varying state space model and linearization of nonlinear systems. The appropriate choice should be evaluated as a part of the identification procedure.

III Nonlinear System Identification

A nonlinear relationship between input and output gives a rich variety of possibilities to describe the system. At the same time, the situation is far too flexible to allow for definite deduction from finite data records.

Even a first-order model without disturbances is specified only up to members in a general infinite-dimensional function space, while the corresponding linear model is characterized in terms of two real numbers.

In most cases, in order to use nonlinear models, some knowledge about the systems nonlinearities is needed in order to be able to create reasonable model structure.

The development of models for nonlinear systems is quite analogous to that described for linear systems. The basic difference is that the predictor function—which is enabling the prediction of future values—becomes a nonlinear function of past observations.

The important difference from a practical point of view is that the potential richness of possibilities makes unstructured "black-box" models unfeasible in most cases. Instead, knowledge about the character of nonlinearities will have to be built into the models. Such structure does not have to be analytical, the nonlinearities can be defined in look-up tables, and the models parameters could be entries in these tables.

There are many methods to examine nonlinear systems, methods such as NARMAX (nonlinear ARMAX) which is an extension of the commonly used parametric linear methods, up to very sophisticated nonlinear models such as Wiener results (kernels) [15] and Korenberg-Billings model [16].

The Volterra-Wiener approach is using the estimation of system kernels from input-output data. This technique employs Laguerre expansions of the kernels and estimates the unknown expansion coefficient via time-averaging of covariance samples [17]. The Wiener kernels can also be estimated using cross correlations [18] and stochastic methods [19].

Referring again to FIG. 6, in step 54, after deciding about the model structure, the basic model is selected out of a set of models according to a predetermined fit criterion. Assuming, for example, that the linear models family is selected, the best model in the family of linear models is picked up.

In step 56 the estimate that results from the model is evaluated. If the estimate is a good estimate according to a predetermined criterion, step 58, the identification of the connection function, is complete, whereas if not, step 54 reexecuted and a different family of models is searched for a best model describing the dynamic system.

Figure 7A:
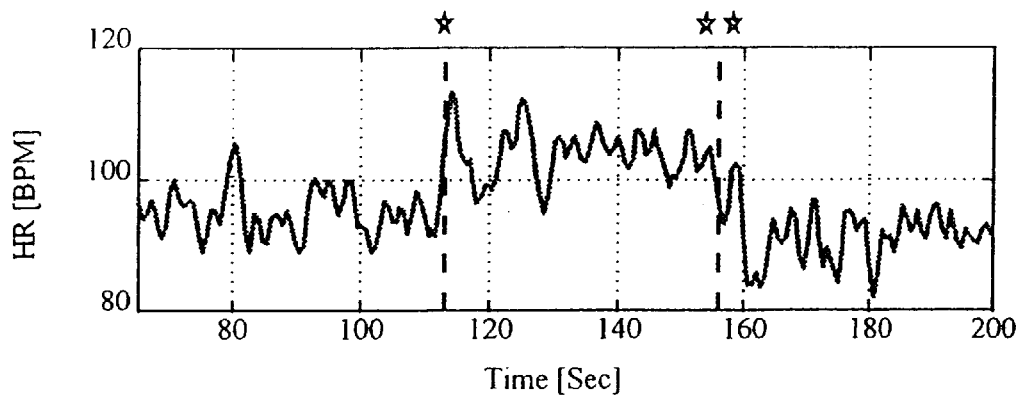
FIGS. 7a–7c is an example of external manipulation, wherein a provocative test, hand grip, is performed for a period of 40 sec in a pregnant woman of 26 weeks gestation age.
Figure 7B:
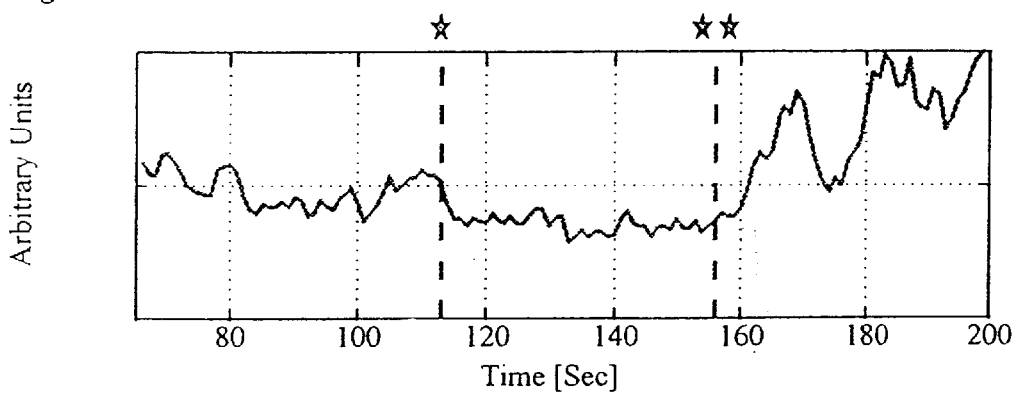
Figure 7C:
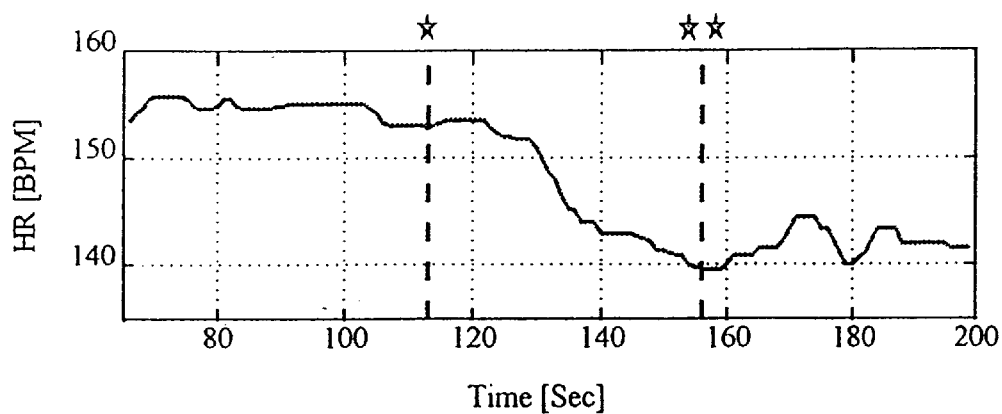

FIGS. 7a–c present the results of a maternal external stimulus provoked by hand grip. During hand grip, there is an increase in maternal HR (FIG. 7a), a decrease in maternal peripheral flow (PPG, FIG. 7b), and, resulting from the exercise, there is a change in fetal HR (FIG. 7c).

Following the exercise there is a fast recovery of maternal HR and flow and a slow recovery of fetal HR. This example shows that external maternal manipulation results in fetal immediate reactivity.

Figure 8A:
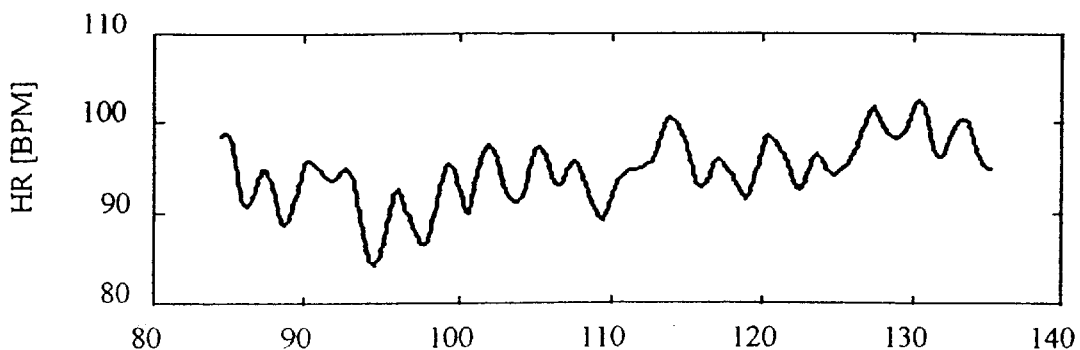
Figure 8B:
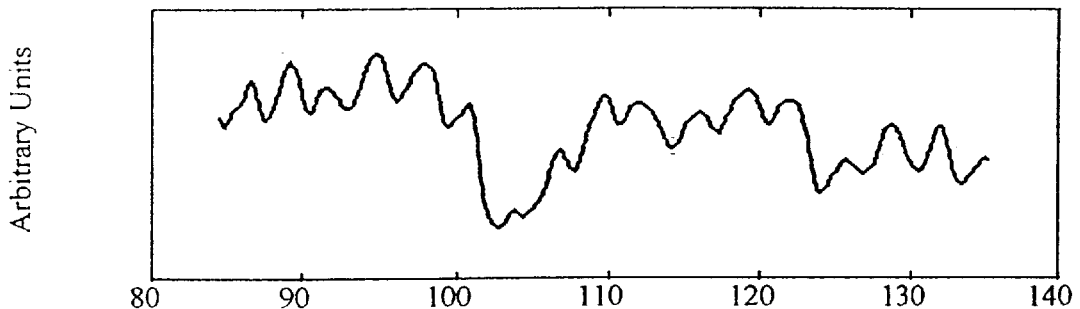
Figure 8C:
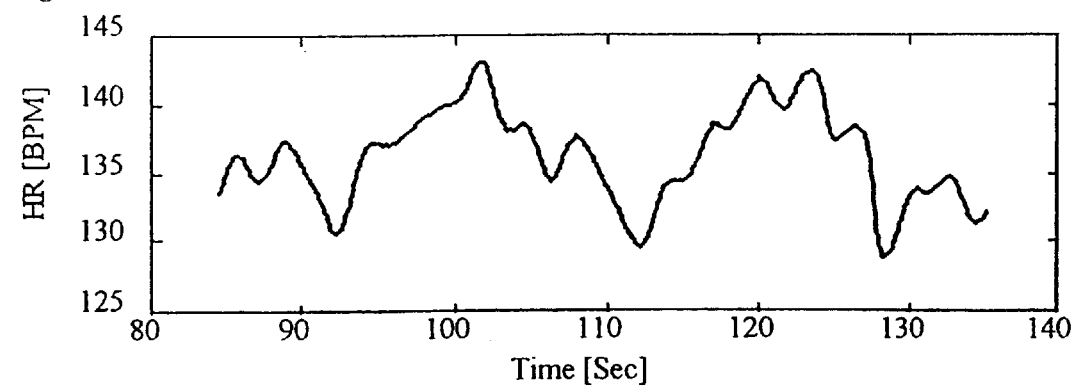

FIGS. 8a–c presents the result of an identification procedure on the following physiological signals: maternal HR (FIG. 8a), maternal peripheral flow (FIG. 8b) obtained by the PPG device—which is a measure of red blood cells concentration, and fetal HR (FIG. 8c). The experiment was performed on a healthy 29 years old multipara having a normal pregnancy of 26 weeks gestation.

A linear model was chosen and it was found that the best model is the Box Jenkins (BJ) model, which is a special case of the general parametric model structure shown in FIG. 8d. As shown in FIG. 8e, the best model was achieved with the following degrees of freedom and parameters: na=2; nb=2; nc=2; nd=2; nk=1.

FIG. 8f shows the quality of this model. One way to find out the quality of a model is to simulate it and compare the model output with measured output. To this end, one selects a portion of the original data that was not used to build the model. The accuracy (or predictivity) of the model in this case was 67.8%.

When dealing with fetal HR the dynamics of the HR results from two sources: internal origin (autonomic nervous system) and external origin. The model in this case should explain the external contribution to fetal HR. Therefore, a 67.8% can be considered a very good fit.

Figure 9:
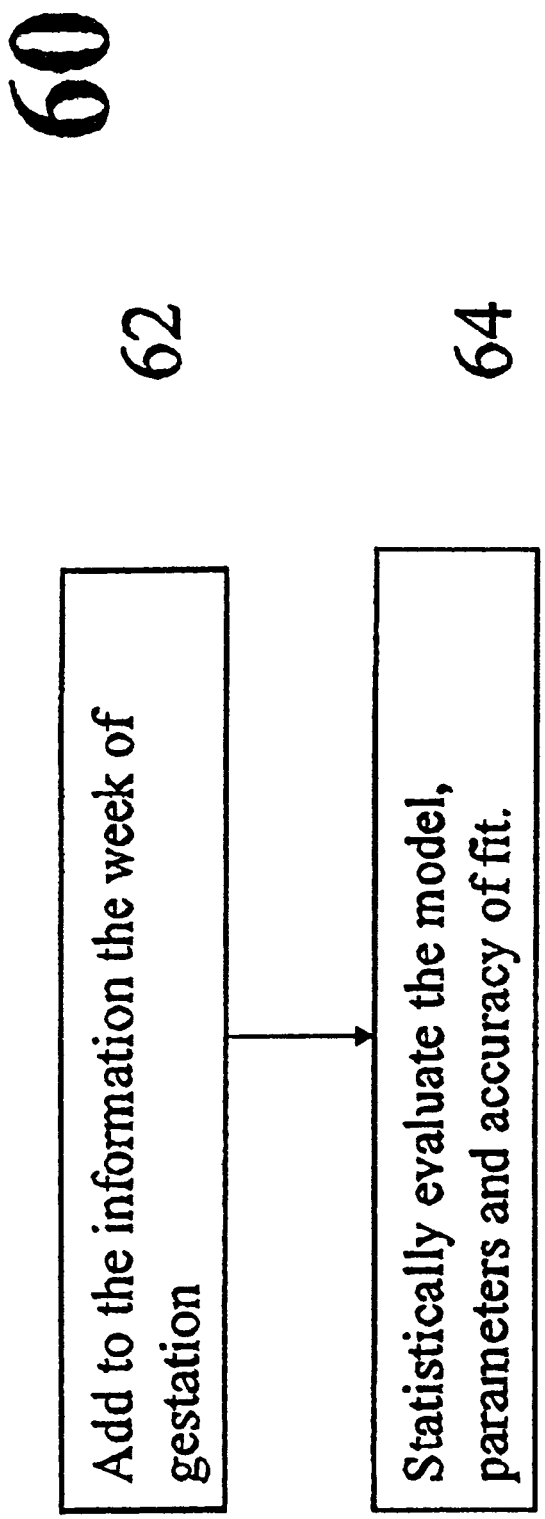
FIG. 9 is the description of the statistical procedure following the identification procedure according to the present invention.

FIG. 9 describes the statistical part of the system, step 60. In step 62 one adds to the information the week of gestation. In step 64 the results of the system identification are evaluated, taking into account the week of gestation, the family model which was used, the specific model within the model structure, the parameters of that specific model and the accuracy of the model. The conditions of the maternal-fetal unit are statistically evaluated for discriminating between high risk or low risk according to a data base previously accumulated. If further interpretation of the test such as the type of the pathology or the level of risk is available it can also be presented.

This present invention is based on the fact that the maternal-placenta-fetal dynamic system is described by open-loop models, as there is no feedback loop between the fetus and the mother.

System identification techniques, where physiological signals obtained from a specific individual in order to create a model for maternal-placenta-fetal regulation, are applied to the recorded data. The search for the appropriate model should preferably start from simple linear models and advance to more complex nonlinear models in case the linear models fail to describe the system to the extent the clinical demands require, that is that the prediction function does not permit an accurate prediction according to the rules established in the beginning of the identification procedure.

As such, system identification is a desirable tool for evaluating the effect of physiological alterations resulting from different pathologies, a change in environmental conditions and physiological stress, such as exercise.

It should be noted that a correlation between maternal pathological conditions are strongly correlated with fetus pathologies.

Pregnancies complicated by chronic hypertension are at increased risk for the development of superimposed preeclampsia, abruptio placentae, and poor perinatal outcome. As for the severity of hypertension in the first trimester, the reported incidence of superimposed preeclampsia ranges from 28.2% to 52% in severe chronic hypertension. On the other hand, the reported incidence for patients with mild hypertension in pregnancy is as low as 4.7% less.

The incidence of abruptio placenta is reportedly increased and ranges between 0.45% and 10% depending on the duration of hypertension [20].

The main risks to the fetus of the eclamptic woman are abruptio placentae, prematuity, intrauterine growth retardation.

Systemic lupus erythematosus (SLE), is a chronic disease with great diversity of clinical manifestations. SLE is associated with an increase in poor pregnancy outcome (from IUGR, stillbirth, spontaneous abortion and preterm delivery). The SLE antibodies are found in 50% of patients with SLE, and are associated with increases risk of pregnancy loss [21].

During pregnancy in the insulin-dependent diabetic woman, periods of maternal hyperglycemia lead to fetal hyperinsulinemia and thus fetal pancreatic stimulation. The resulting fetal hyperinsulinemia is associated with excessive fetal growth and other morbidities. Congenital malformations are two times more common in the offspring of insulin-dependent diabetic woman. Reduced uterine blood flow is thought to contribute to the increased incidence of intrauterine growth restriction (IUGR) observed in pregnancies complicated by diabetic vasculopathy [22].

Placenta blood flow is very sensitive to changes in maternal hemodynamic status. Administering anesthesia, either regional or general, to a parturient must involve efforts to avoid fetal compromise secondary to hypotension or intense uterine vasoconstriction. The supine position is avoided at all times, especially during anesthesia. Maternal compensation for the efforts of vena caval compression that normally occur in the absence of anesthesia can be significantly impaired when anesthesia depresses vascular reflex mechanisms. Laboring patients with epidural analgesia requiring nursing in a full or semilateral position at all times. General anesthesia is induced with the patient in a 15-degree left lateral tilt. Additionally, sudden alterations of blood pressure are avoided. Failure to treat hypotension will rapidly produce changes in the fetal heart rate tracing suggestive of hypoxia [23].

Thus, it is evident that maternal pathological conditions are strongly correlated with fetus pathologies, whereas the reason for that is the dynamic open loop system characterizing the maternal-placenta-fetus.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

LIST OF REFERENCES CITED

1. Williams Obstetrics, Pritchard and Mc Donald eds., Appleton-Century-Crofts, New York, 1980.
2. Northe R. A., Ferrier C, Long D, Townend K and Pinkus-Smith P. *Uterine artery and flow velocity waveforms in the second trimester for the prediction of preeclampcia and fetal growth retardation*. Obstetrics and Gynecology Vol 83 pp. 378–386, 1994.
3. Gusdon J P Jr, Anderson S G, May W J. *A clinical evaluation of the "roll-over test" for pregnancy induced hypertension*. Am J obstet Gynecol 1: 127(1): 1–3, January 1997.
4. Eneroth-Grimforms E, Bevegard S, Nilsson Ba. *Evaluation of three simple physiological tests as predictors of pregnancy-induced hypertension. A pilot study.* Acta Obstet Gynecol Scand; 67(2):109–113, 1988.
5. Peck T M *A simple test for predicting pregnancy-induced hypertension.* Obstet Gynecol 50(5):615–617 November 1977.
6. Andersen G J. *The roll over test as a screening procedure for gestational hypertension.* Aust N Z J Obstet Gynecol 20(3): 144–150, August 1980.
7. Baker P N, Johnson I R. *The use of the hand-grip test for predicting pregnancy—induced hypertension.* Eur J Obstet Gynecol Reprod Biol 56(3):169–172, September 1994.
8. Degani S, Abinader E, Eibschitz I, Oettinger M, Shapiro I, Sharf M. *Isometric exercise test for predicting gestational hypertension.* Obstet Gynecol 65(5):652–654, May 1985.
9. Loyke HF. *Cold pressor test as a predictor of the severity of hypertension.* Sounth Med J; 88(3):300–304, May 1995.
10. Chang C, Zhang J. *The analysis of relationship between fetal stress and blood dynamics in fetal vessels and placenta bed vessels.* Chung Hau Fu Vhan Tsa Chin 31(1)46:15–17, January 1996.
11. Cottrill C M, Jeffers Lo J, Ousey J C, McGladdery A J, Rickefts S W, Silver M, Rossdale P D. *The placenta as a determinant of fetal well being in normal and abnormal pregnancies.* J. Reprod Fertil Suppl 44:591–601, 1991.
12. Fairlie F M. *Doppler flow velocimetry in hypertension in pregnancy.* Clin Perinatol 18(4):749–778, December 1991.
13. Badalian S S. *Nature and mechanism of hemodynamic changes in fetuses of mothers with various types of diabetes mellitus.* Akush Ginekol Mosk 9:39–42, September 1989.
14. Ljung L. *System Identification; theory for the user.* Prentice-Hall Inc., Englwood Cliffs, N.J. Edited by T. Kailath, 1987.
15. Wiener N: *Nonlinear problems in random theory.* New York Wiley; 1958.
16. Sun H. H and Shi J. H. *New algorithm for Korenberg-Billings model of nonlinear system identification.* In: Advanced method of physiological system modeling: Vol II. New-York: Plenum Publishing; 1989: pp. 179–200.
17. Marmaralis V Z: *Identification of nonlinear biological systems using Laguerre expansion of kernels.* Ann Biomed Eng, 21:573–589, 1993.
18. Schetzen M, Lee Y W: *Measurements of the Wiener kernels of nonlinear system by cross correlation*: Int J control, 2: 237–254, 1965.
19. Goussard Y. *Wiener kernel estimation: A comparison of cross correlation and stochastic approximation methods.* In: advanced methods of physiological system modeling: Vol I. Los Angeles, Calif.:USC Biomedical Simulations Resources; 1987: pp. 289–302.
20. Sibal B M, Abdella T N, Anderson G D. *Pregnancy outcome in 211 patients with mild chronic hypertension.* Obstet & Gynecol 78:451, 1991.
21. Branch D W, Scott J R et al. *Obsterics complications associated with the lupus anticoagulant.* N Eng J Med 313:1322, 1985.
22. *Uteroplacental blood flow in diabetic pregnancy.* Am J Obstet Gynecol 144:298, 1982.
23. Corke CB. *Complication of obstetric anesthesia.* In Francis M J (ed) Obsteric anesthesia: The complicated patient. F. A. Davis, 1990.

These documents are incorporated by reference as if fully set forth herein.

What is claimed is:

1. A method of determining the well being of a placenta in a pregnant woman having a maternal-placenta-fetal system, the method comprising the steps of:
   (a) simultaneously monitoring selected maternal and fetal physiological signals;
   (b) using said physiological signals for identifying a mathemaical model describing the maternal-placenta-fetal system, and mathematical parameters describing said model; and
   (c) determining, according to said mathematical model and said mathematical parameters describing said mathematical model, the well being of the placenta.

2. The method of claim 1, wherein while simultaneously monitoring said selected maternal and fetal physiological signals the pregnant woman is provoked by an external stimulus.

3. The method of claim 1, wherein said physiological signals are selected from the group consisting of ECG, BP, $PO_2$, $PCO_2$, blood flow, blood velocity, blood volume, heart rate, systolic blood pressure, diastolic blood pressure, systolic/diastolic blood pressure ratio, resistance index, pulsatility index, thermal index.

4. The method of claim 1, wherein said mathematical model is selected from the group consisting of nonparametric models, parametric models, polynominal representation, simple autoregressive model, ARMAX model structure, output error structure, Box-Jenkins model structure, general parametric model structure, state space representation, linear time-varying models, time-invariant model, nonlinear models, nonlinear ARMAX, Wiener kernels model, Korenberg-Billings model and Volterra-Wiener model.

5. The method of claim 1, wherein said step of identifying said mathematical model is effected by identifying a best mathematical model describing the maternal-placenta-fetal system, said best mathematical model is selected out of a plurality of available mathematical models and according to predetermined criteria.

6. A method of determining the well being of a fetus in a pregnant woman having a maternal-placenta-fetal system, the method comprising the steps of:
   (a) simultaneously monitoring selected maternal and fetal physiological signals;
   (b) using said physiological signals for identifying a mathematical model describing the maternal-placenta-fetal system, and mathematical parameters describing said mathematical model; and
   (c) determining, according to said mathematical model and said mathematical parameters describing said mathematical model, the well being of the fetus.

7. The method of claim 6, wherein while simultaneously monitoring said selected maternal and fetal physiological signals the pregnant woman is provoked by an external stimulus.

8. The method of claim 6, wherein said physiological signals are selected from the group consisting of ECG, BP, $PO_2$, $PCO_2$, blood flow, blood velocity, blood volume, heart rate, systolic blood pressure, diastolic blood pressure, systolic/diastolic blood pressure ratio, resistance index, pulsatility index, thermal index.

9. The method of claim 6, wherein said mathematical model is selected from the group consisting of nonparametric models, parametric models, polynominal representation, simple autoregressive model, ARMAX model structure, output error structure, Box-Jenkins model structure, general parametric model structure, state space representation, linear time-varying models, time-invariant model, nonlinear models, nonlinear ARMAX, Wiener kernels model, Korenberg-Billings model and Volterra-Wiener model.

10. The method of claim 6, wherein said step of identifying said mathematical model is effected by identifying a best mathematical model describing the maternal-placenta-fetal system, said best mathematical model is selected out of a plurality of available mathematical models and according to predetermined criteria.

11. A method of determining a maternal-fetus relation in a pregnant woman having a maternal-placenta-fetal system, the method comprising the steps of:
   (a) simultaneously monitoring selected maternal and fetal physiological signals;
   (b) using said physiological signals for identifying a mathematical model describing the maternal-placenta-fetal system, and mathematical parameters describing said mathematical model; and
   (c) determining, according to said mathematical model and said mathematical parameters describing said mathematical model, the maternal-fetus relation.

12. The method of claim 11, wherein while simultaneously monitoring said selected maternal and fetal physiological signals the pregnant woman is provoked by an external stimulus.

13. The method of claim 11, wherein said physiological signals are selected from the group consisting of ECG, BP, $PO_2$, $PCO_2$, blood flow, blood velocity, blood volume, heart rate, systolic blood pressure, diastolic blood pressure, systolic/diastolic blood pressure ratio, resistance index, pulsatility index, thermal index.

14. The method of claim 11, wherein said mathematical model is selected from the group consisting of nonparametric models, parametric models, polynominal representation, simple autoregressive model, ARMAX model structure, output error structure, Box-Jenkins model structure, general parametric model structure, state space representation, linear time-varying models, time-invariant model, nonlinear models, nonlinear ARMAX, Wiener kernels model, Korenberg-Billings model and Volterra-Wiener model.

15. The method of claim 11, wherein said step of identifying said mathematical model is effected by identifying a best mathematical model describing the maternal-placenta-fetal system, said best mathematical model is selected out of a plurality of available mathematical models and according to predetermined criteria.

16. A system for monitoring of a pregnancy in a pregnant woman having a maternal-placenta-fetal system, the system comprising:
   (a) at least one monitoring device for simultaneously monitoring selected maternal and fetal physiological signals; and
   (b) a computerized system being in communication with each of said at least one monitoring devices for identifying a mathematical model describing the maternal-placenta-fetal system, and mathematical-parameters describing said mathematical model.

17. The system of claim 16, wherein said physiological signals are selected from the group consisting of ECG, BP, $PO_2$, $PCO_2$, blood flow, blood velocity, blood volume, heart rate, systolic blood pressure, diastolic blood pressure, systolic/diastolic blood pressure ratio, resistance index, pulsatility index, thermal index.

18. The system of claim 16, wherein said mathmatical model is selected from the group consisting of nonparametric models, parametric models, polynominal representation, simple autoregressive model, ARMAX model structure, output error structure, Box-Jenkins model structure, general parametric model structure, state space representation, linear time-varying models, time-invariant model, nonlinear models, nonlinear ARMAX, Wiener kernels model, Korenberg-Billings model and Volterra-Wiener model.

19. The system of claim 16, wherein said mathematical model is a best mathematical model describing the maternal-placenta-fetal system, said best mathematical model is selected out of a plurality of available mathematical models and according to predetermined criteria.

* * * * *